(12) United States Patent
Stroot

(10) Patent No.: US 10,976,327 B1
(45) Date of Patent: Apr. 13, 2021

(54) METHODS AND SYSTEMS FOR CONTROLLING OXIDATIVE STRESS

(71) Applicant: Western Autotroph Company LLC, Parker, CO (US)

(72) Inventor: Peter Stroot, Parker, CO (US)

(73) Assignee: Western Autotroph Company LLC, Liberty Lake, WA (US)

( * ) Notice: Subject to any disclaimer, the term of this patent is extended or adjusted under 35 U.S.C. 154(b) by 160 days.

(21) Appl. No.: 16/002,953

(22) Filed: Jun. 7, 2018

Related U.S. Application Data

(63) Continuation of application No. 14/929,124, filed on Oct. 30, 2015, now Pat. No. 9,995,758.

(60) Provisional application No. 62/073,876, filed on Oct. 31, 2014.

(51) Int. Cl.
  *G01N 33/84* (2006.01)
  *G01N 21/78* (2006.01)
  *G01N 21/64* (2006.01)

(52) U.S. Cl.
  CPC ............. *G01N 33/84* (2013.01); *G01N 21/78* (2013.01); *G01N 2021/6439* (2013.01); *G01N 2800/7009* (2013.01)

(58) Field of Classification Search
  CPC ................... G01N 33/84; G01N 21/78; G01N 2021/6439; G01N 2800/7009
  See application file for complete search history.

(56) References Cited

U.S. PATENT DOCUMENTS

| | | | |
|---|---|---|---|
| 9,995,758 B1* | 6/2018 | Stroot | G01N 33/84 |
| 2008/0033258 A1* | 2/2008 | Dudley | G01N 33/6815 600/300 |
| 2016/0376650 A1* | 12/2016 | Baranova | A61P 3/06 424/172.1 |
| 2017/0122954 A1* | 5/2017 | Lebedeva | C12Q 1/02 |
| 2017/0219598 A1* | 8/2017 | Fu | A61K 9/0019 |

* cited by examiner

*Primary Examiner* — Brian J. Sines
(74) *Attorney, Agent, or Firm* — Knobbe, Martens, Olson & Bear LLP

(57) ABSTRACT

The present application describes methods and systems for measuring and controlling oxidative stress in animals and humans. The degree of oxidative stress can be measured directly by inducing all of the blood cells to produce excessive reactive oxygen species (ROS) by exposure to an elevated concentration sulfide or other ROS inducing chemical and measuring the fluorescence intensity of a fluorescent dye or color intensity of dye that reacts with ROS. Oxidative stress can be reduced by reducing dietary sulfur, consumption of a methanogenic probiotic, or apheresis methods to replace ROS-positive blood cells with normal blood cells. Plasma oxidative stress can be compared in venous and arterial blood samples to evaluate small vessel disease. Oxidative stress can be increased by increasing dietary sulfur or the use of an intravenous method that exposes blood cells to an elevated blood concentration of sulfide or other ROS inducing chemical.

17 Claims, 3 Drawing Sheets

METHODS AND SYSTEMS FOR CONTROLLING OXIDATIVE STRESS

CROSS-REFERENCE TO RELATED APPLICATIONS

This application is a continuation application of U.S. patent application Ser. No. 14/929,124, filed Oct. 30, 2015, which claims the priority benefit under 35 U.S.C. § 119(e) of U.S. Provisional Application No. 62/073,876, filed Oct. 31, 2014, the entireties of which are hereby incorporated by reference herein. Any and all applications identified in a priority claim in the Application Data Sheet, or any correction thereto, are hereby incorporated by reference herein and made a part of the present disclosure.

BACKGROUND

Field

This application relates generally to human health, animal health, biochemical production and/or the like, and more specifically, to methods and systems for measuring and controlling oxidative stress in animals and humans by, inter alia, controlling the percent of blood cells that are induced to produce reactive oxygen species (ROS).

Description of the Related Art

Certain hypotheses suggest that oxidative stress is caused by the consumption of elevated levels of inorganic sulfur. Ultra-exogenous sulfide formation (USF) is caused by the combination of high abundance of sulfate reducing bacteria (SRB) and the consumption of elevated levels of inorganic sulfur. USF results in exposure of blood cells in the right colonic capillary network to elevated sulfide concentration, which induces a reactive oxygen species (ROS) response.

SUMMARY

According to some embodiments, a method for measuring a degree of blood oxidative stress in a subject comprises collecting a first sample of blood from the subject, collecting a second sample of blood from the subject, wherein each of the first and second samples of blood contains plasma, adding a first agent to the second sample, the first agent being configured to induce reactive oxygen species (ROS) in blood cells of the second sample, reacting the second sample after the first agent has been added to the second sample for a first predetermined time period, the first predetermined time period being sufficient to induce production of ROS in blood cells of the second sample, reacting the first sample of blood for the first predetermined time period during a first reacting step, diluting the first and second samples following the reacting steps to reducing a concentration of ROS in the plasma of each of the first and second samples, reacting each of the first and second samples, after dilution, for a second predetermined time period during a second reacting step, isolating the plasma of each of the first and second samples following the second reacting step, adding a second agent to each of the first and second samples following the isolating step, wherein adding the second agent at least partially reacts with ROS present in the plasma of each of the first and second samples, measuring a level in each of the first and second samples indicative of reaction product formed in the plasma after the second agent has reacted with ROS in each of the first and second samples and comparing the level of reaction product of the first sample to the level of reaction product of the second sample, wherein the comparison step is indicative of the degree of blood oxidative stress in a subject.

According to some embodiments, reacting comprises incubation. In some embodiments, the first predetermined time period is equal or greater than the second predetermined time period. In some embodiments, the first predetermined time period is 30 minutes to 2 hours. In one embodiment, the second predetermined time period is 5 to 30 minutes.

According to some embodiments, the isolating step is performed using centrifugation or filtration. In some embodiments, filtration comprises using membrane filtration.

According to some embodiments, the first agent comprises at least one of sodium hydrogen sulfide (NaHS), 4-demethoxydaunorubicin (idarubicin) and tert-Butyl hydroperoxide (TBHP).

According to some embodiments, the second agent comprises a colorimetric dye (e.g., xylenol orange and ferric iron solution, other colorimetric dyes, etc.). In some embodiments, the second agent comprises a fluorescent dye (dihydrodichlorofluorescein, dihydrorhodamine, etc.).

According to some embodiments, the method further comprises providing guidance to the subject for treatment. In some embodiments, the guidance comprises at least one of the following: apheresis, other blood replacement procedures, dietary changes and pharmaceutical correction.

According to some embodiments, the method further comprises treating the subject if the degree of blood oxidative stress is above a threshold or if the degree of blood oxidative stress is indicative of disease. In some embodiments, treating the subject comprises at least one of the following: apheresis, other blood replacement procedures, dietary changes and pharmaceutic correction.

According to some embodiments, a kit for measuring a degree of blood oxidative stress in a subject includes a first agent, and second agent, wherein the first and second agents are used to perform a method as indicated herein.

According to some embodiments, the kit further comprises first and second containers (e.g., vials) for containing the first and second samples of blood, respectively. In some embodiments, the kit further comprises instructions for use, wherein the instructions for use provide instructions to a user in accordance with the steps of the various methods disclosed herein.

According to some embodiments, a method for measuring a degree of small vessel disease in a subject comprises collecting a first sample of arterial blood from the subject, collecting a second sample of venous blood from the subject, wherein each of the first and second samples of blood contains plasma, isolating the plasma of each of the first and second samples, adding a second agent to each of the first and second samples following the isolating step, wherein adding the second agent at least partially reacts with ROS present in the plasma of each of the first and second samples, measuring a level in each of the first and second samples indicative of reaction product formed in the plasma after the second agent has reacted with ROS in each of the first and second samples and comparing the level of reaction product of the first sample to the level of reaction product of the second sample, wherein the comparison step is indicative of the degree of small vessel disease in a subject.

According to some embodiments, the present application describes, inter alia, methods and systems for measuring and controlling oxidative stress in animals and humans. In some embodiments, the degree of oxidative stress can be measured directly by inducing all of the blood cells that are capable of producing excessive reactive oxygen species (ROS) to produce ROS by exposure to an elevated concentration of sulfide and/or other ROS inducing chemicals and measuring the fluorescence intensity of a fluorescent dye that reacts with ROS or color intensity of a dye that reacts with ROS. In some embodiments, a dilution of this sample is used to develop a standard curve that is used to measure the degree of oxidative stress in the original sample. In one embodiment, the plasma ROS concentration is compared in venous and arterial blood samples to evaluate small vessel disease and/or other diseases or indications.

According to some embodiments, oxidative stress is reduced by management of the consumption (e.g., reduction) of inorganic sulfur to meet the daily minimal requirement and/or the consumption of a methanogenic probiotic that reduces the abundance of the sulfate reducing bacteria in the large intestine and associated ultra-exogenous sulfide (USF).

According to some embodiments, oxidative stress is increased by consumption of inorganic sulfur that exceeds the daily minimal requirement by diet or supplementation and/or an intravenous method is used to expose blood cells to an elevated concentration of sulfide or other ROS-inducing chemical that induces the production of reactive oxygen species (ROS).

According to some embodiments, mechanisms involved in USF provide insight into methods for reducing or increasing oxidative stress in animals and humans. In addition, a simple method can be used to measure the percent of ROS-positive blood cells.

According to some embodiments, the ability to induce ROS-positive blood cells can be used in a method for measuring the existing percent of ROS-positive blood cells and for measuring the percent of ROS-positive blood cells after attempts at reducing or increasing oxidative stress. In some embodiments, several methods for reducing oxidative stress are described to reduce ultra-exogenous sulfide formation (USF), one of the primary causes of generating ROS-positive blood cells.

According to some embodiments, a modified diet that meets the minimal daily requirements for inorganic sulfur is managed by the use of a smart phone application and/or some other computing device or system that maintains a daily cumulative measure of the inorganic sulfur consumed by using user input data for the type and amount of food.

According to some embodiments, a methanogenic probiotic may be used to provide a hydrogen competitor for the sulfate reducing bacteria (SRB) in the large intestine. In some embodiments, over time, the methanogenic probiotic can reduce the abundance of the SRB and reduce USF, which can also beneficially allow dietary freedom to consume foods with inorganic sulfur content that exceeds the daily minimal requirement.

According to some embodiments, the increase of oxidative stress may be necessary or helpful to protect animals and humans from catalase-negative pathogens. In some embodiments, a diet with higher levels of inorganic sulfur may promote USF. In some embodiments, a more rapid approach utilizes an intravenous method to expose blood cells to elevated levels of sulfide or ROS inducing chemicals, which are required to induce the ROS response.

According to some embodiments, a test that uses a fluorescent dye that reacts with ROS in the blood is used to estimate the percent of ROS-positive blood cells. In some embodiments, a blood sample could be collected and exposed to an elevated concentration of sulfide or other ROS inducing chemical in order to induce all of the blood cells to produce excessive levels of ROS. In some embodiments, a blood sample with 100% of the blood cells that are ROS-positive can then be used to create a dilution series using either inactivated blood or a suitable diluent, such as saline solution. In some embodiments, a standard curve is generated that relates the whole blood fluorescence to the percent of ROS-positive blood cells. In this way, the percent ROS-positive blood cells can be advantageously evaluated in a step-wise manner to ensure that the human or animal doesn't exceed the targeted percent ROS-positive blood cells.

According to some embodiments, chronic oxidative stress can be reduced to healthier levels by either reducing the daily consumption of inorganic sulfur to just meet the minimal daily requirement or the consumption of a methanogenic probiotic. In some embodiments, in addition to the concern regarding the role of oxidative stress with multiple diseases and cancers, antibiotic resistance in some bacteria has been linked to oxidative stress. In some embodiments, the reduction of oxidative stress in humans or animals suffering from a pathogenic infection may prove to be advantageous for antibiotic therapy. In some embodiments, the reduction of oxidative stress in humans may also be advantageous when evaluating new pharmaceuticals, since excessive ROS may oxidize the pharmaceuticals rendering them non-therapeutic.

According to some embodiments, dietary management of inorganic sulfur is hampered by the lack of food testing data and tools, such as an application for a smart phone application or other "smart" device (e.g., PDA, PC or other computer, etc.). Currently, in some embodiments, the FDA does not require the disclosure of inorganic or organic sulfur content in foods. In some embodiments, inorganic sulfur, such as sulfiting agents, is commonly used as a food preservative in the United States and Europe. With food testing data available, the management of USF can become simpler with the use of a smart phone application or the like, which can provide daily cumulative total of consumed inorganic sulfur and guidance for future meals. In some embodiments, an analysis of animal feed consumption may also reveal excessive inorganic sulfur consumption resulting in oxidative stress. In some embodiments, a specially-formulated feed containing lower levels of inorganic sulfur may reduce oxidative stress in animals caused by USF.

According to some embodiments, consumption of a suitable methanogenic probiotic can provide a means for reducing oxidative stress. For example, *Methanobrevibacter* spp. are methanogens that are commonly found in the human gut, but it is absent in individuals that consume elevated levels of inorganic sulfur. In some embodiments, this exclusion is most likely due to *Methanobrevibacter* spp. being catalase-negative, which makes them vulnerable to oxidative stress. In some embodiments, the ideal or preferred methanogenic probiotic would be a catalase-positive *Methanobrevibacter* strain, but higher levels of catalase-negative *Methanobrevibacter* strain may also be effective. In some embodiments, for example, for animals that do not have the option of a modified feed to reduce USF, a methanogen commonly found in the animal gut could be provided as a probiotic.

According to some embodiments, apheresis methods could be used to reduce oxidative stress by the replacement of ROS-positive blood cells with normal blood cells.

According to some embodiments, guidelines for healthy and unhealthy levels of oxidative stress are possible by comparison of percent ROS-positive blood cells to humans with defined health conditions.

According to some embodiments, small vessel disease (SVD) may be detected by comparing the plasma ROS concentration (BlOSvalue) in venous and arterial blood samples.

According to some embodiments, low levels of oxidative stress may be beneficial. In some embodiments, the impact of virulent catalase-negative pathogens, such as *Enterococcus faecium* and Ebola virus, may be reduced by a population, animal or human, that maintains a low level of oxidative stress. In some embodiments, in cases where the consumption of inorganic sulfur meets the minimal daily requirement to maintain health, an increase in the dietary consumption of inorganic sulfur will promote USF. In some embodiments, the consumption of a supplement containing higher levels of sulfate that releases in the large intestine would be a more attractive option when food with higher levels of inorganic sulfur is not available.

According to some embodiments, for the rapid increase of oxidative stress, intravenous (IV) method for exposing blood cells to elevated sulfide, such as NaHS, or other ROS inducing chemicals will induce the ROS response. In some embodiments, in such a method, the percent of ROS-positive blood cells is a function of the percent blood flow and the time. In some embodiments, greater times can result in higher percent ROS-positive blood cells for greater oxidative stress. In some embodiments, for example, for an IV provided to the arm, an assumed blood flow rate of 432 ml/min represents 9% of the cardiac output. In some embodiments, an exposure time of about 2.5 minutes would induce the excessive production of ROS in about 20% of the blood cells.

BRIEF DESCRIPTION OF THE DRAWINGS

These and other features, aspects and advantages of the present inventions are described with reference to drawings of certain preferred embodiments, which are intended to illustrate, but not to limit, the present inventions. It is to be understood that the attached drawings are provided for the purpose of illustrating concepts of the present inventions and may not be to scale.

DETAILED DESCRIPTION

According to some embodiments, mechanisms involved in USF provide insight into methods for reducing or increasing oxidative stress in animals and humans. In addition, a simple method can be used to measure the percent of ROS-positive blood cells.

According to some embodiments, the ability to induce ROS-positive blood cells can be used in a method for measuring the existing percent of ROS-positive blood cells and for measuring the percent of ROS-positive blood cells after attempts at reducing or increasing oxidative stress. In some embodiments, several methods for reducing oxidative stress are described to reduce ultra-exogenous sulfide formation (USF), the primary cause of generating ROS-positive blood cells. In some embodiments, a modified diet that meets the minimal daily requirements for inorganic sulfur is managed by the use of a smart phone application that maintains a daily cumulative measure of the inorganic sulfur consumed by using user input data for the type and amount of food.

According to some embodiments, a methanogenic probiotic may be used to provide a hydrogen competitor for the sulfate reducing bacteria (SRB) in the large intestine. In some embodiments, over time, the methanogenic probiotic will reduce the abundance of the SRB and reduce USF, which can also allow dietary freedom to consume foods with inorganic sulfur content that exceeds the daily minimal requirement. In some embodiments, the increase of oxidative stress may be necessary or helpful to protect animals and humans from catalase-negative pathogens. In some embodiments, a diet with higher levels of inorganic sulfur may promote USF. In some embodiments, a more rapid approach utilizes an intravenous method to expose blood cells to elevated levels of sulfide or other ROS inducing chemicals, which are required to induce the ROS response.

Measurement of Oxidative Stress

Figure 1:
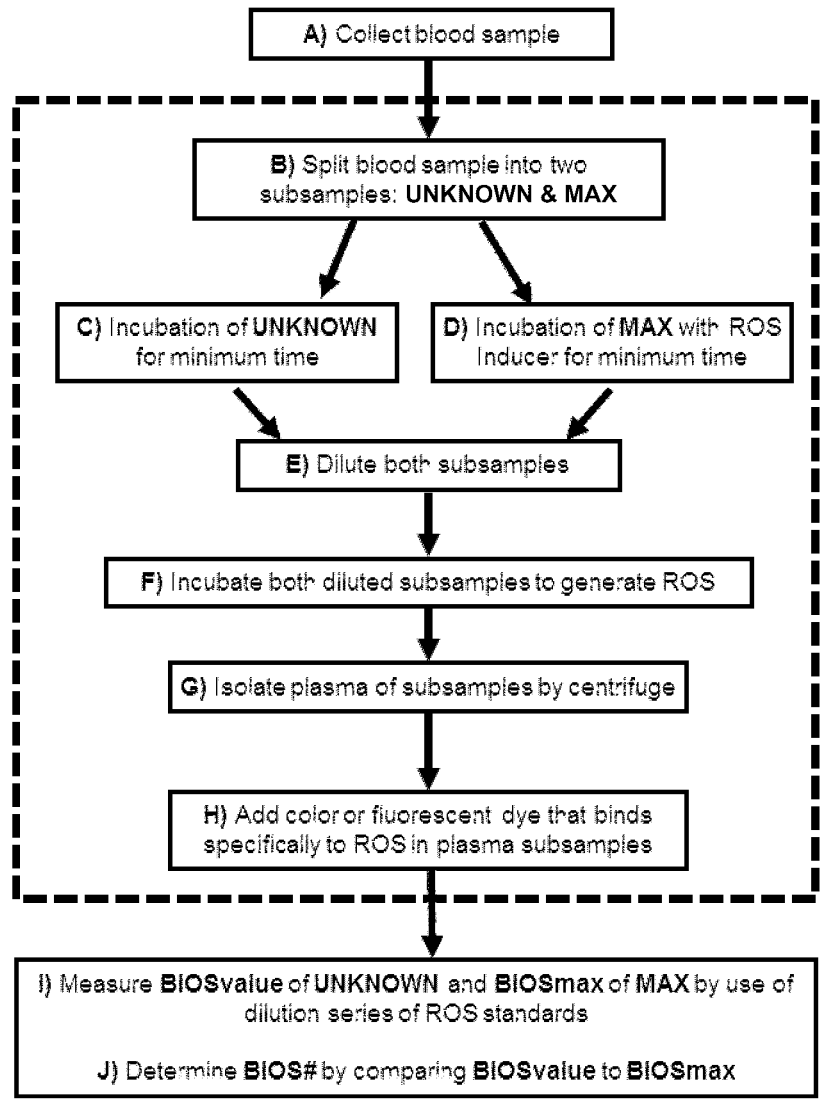
FIG. 1 is a flowchart illustrating a method for determining BlOS for evaluating blood oxidative stress according to one embodiment.

According to some embodiments, a test that uses a fluorescent dye that reacts with ROS in the blood is used to estimate the percent of ROS-positive blood cells. In some embodiment, for example, as illustrated in the flowchart of FIG. 1, a blood sample can be collected using conventional methods (1A). The blood sample is split into two subsamples (1B), referred to as UNKNOWN and MAX in FIG. 1, by transferring equal volumes into new vials used for subsequent centrifugation. Both subsamples can be incubated under temperature and mixing conditions that promote ROS production (1C and 1D), while the MAX subsample includes a ROS inducer.

With continued reference to the embodiment of FIG. 1, after incubation at the minimum time necessary for the ROS inducer to reach maximum rate of ROS production, both subsamples can be diluted (e.g., by 100 fold or more) with a solution (1E) that maintains cell viability. Both diluted subsamples are incubated under conditions that promote ROS production (1F) for a short period (e.g., a few minutes) to generate new ROS that diffuses into the plasma. In some arrangements, following this second incubation step, both subsamples are centrifuged (1G) to separate the plasma from the blood cells. The isolated plasma is transferred to a tube or other container and a ROS-specific dye, fluorescent or color, is added (1H). After sufficient time for the ROS-specific dye to react with the plasma ROS, the ROS concentration in both subsamples (BlOSvalue and BlOSmax) is measured using a fluorimeter or colorimeter by comparing the fluorescent or color intensity to a dilution series using ROS concentration standards (1I).

In some embodiments, the BlOS # is determined by comparing the BlOSvalue of the UNKNOWN subsample to the BlOSmax of the MAX subsample (1J). Alternatively, the MAX subsample could be serially diluted in order to develop an internal standard curve for measuring the relative ROS concentration of UNKNOWN subsample. In some embodiments, a kit (e.g., a commercial test kit) can be used to perform such a test. The various components and steps that can be included in one embodiment of a commercial kit for measuring BlOS # are included within the box defined by the dashed line in FIG. 1. However, additional or fewer components and/or steps can be included in a kit, as desired or required. Accordingly, in some embodiments, the percent ROS-positive blood cells can be advantageously evaluated in a step-wise manner to ensure that the human or animal being evaluated does not exceed the targeted percent ROS-positive blood cells.

Figure 2:
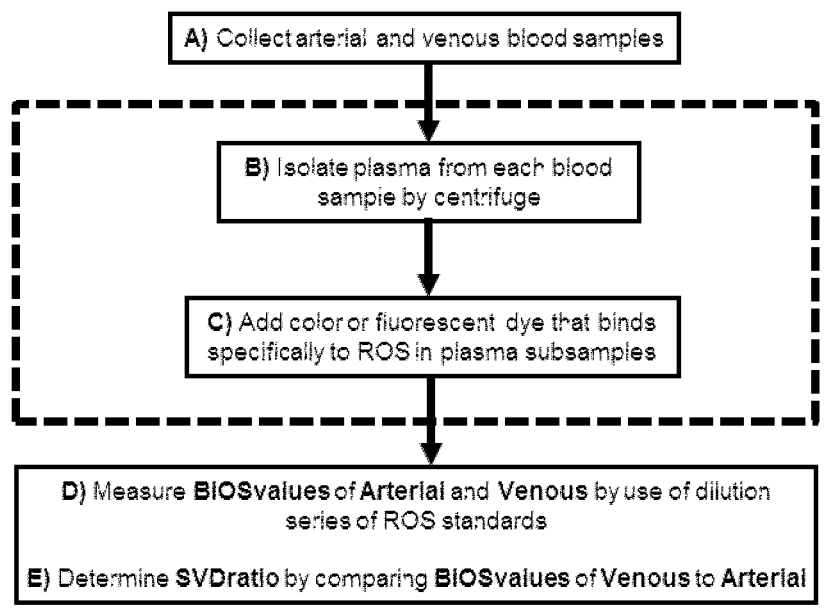
FIG. 2 is a flowchart illustrating a method for determining SVDratio for evaluating small vessel disease according to one embodiment.

According to some embodiments, small vessel disease (SVD) or a similar vascular disorder may be detected by comparing the plasma ROS concentration (e.g., BlOSvalue) in venous and arterial blood samples. As illustrated by the embodiment of FIG. 2, arterial and venous blood samples are collected using conventional methods (2A). Each blood sample can be promptly centrifuged (e.g., immediately after collection) to isolate the plasma, which is transferred to a test tube container (2B). A color or fluorescent dye that reacts specifically to ROS can be added to each subsample (2C). After sufficient time is provided for the dye to react with the ROS in each subsample, BlOSvalues can be measured using a fluorimeter or colorimeter in each subsample by comparison to a standard dilution series of ROS standards (2D). In some arrangements, the SVDratio is determined by comparing the BlOSvalues of the Venous sample to the Arterial Sample (2E).

A kit can be developed in order to determine the SVDratio. In some embodiments, the components and steps of a commercial kit for measuring SVDratio include the various features of the box defined by the dashed line in FIG. 2. However, additional or fewer components and/or steps can be included in a kit, as desired or required. In some embodiments, comparison of the plasma concentration of venous and arterial blood samples may reveal SVD when the ratio (SVDratio) is much greater than 1.5. SVD combined with high percent ROS-positive blood cells can result in acute localized oxidative stress in organs and extremities. In some embodiments, measurement of SVDratio may also be used to monitor the effectiveness of various treatments including, without limitation, diet, exercise, pharmaceuticals and/or the like.

Reduction of Oxidative Stress

According to some embodiments, chronic oxidative stress can be reduced to healthier levels by either reducing the daily consumption of inorganic sulfur to meet the minimal daily requirement or the consumption of a methanogenic probiotic. In some embodiments, in addition to the concern regarding the role of oxidative stress with multiple diseases (e.g., cancers, inflammatory diseases, etc.), antibiotic resistance in some bacteria has been linked to oxidative stress. In some embodiments, the reduction of oxidative stress in humans or animals suffering from a pathogenic infection may prove to be advantageous for antibiotic therapy. In some embodiments, the reduction of oxidative stress in humans may also be advantageous when evaluating new pharmaceuticals, since excessive ROS may oxidize the pharmaceuticals rendering them non-therapeutic.

According to some embodiments, dietary management of inorganic sulfur is hampered by the lack of food testing data and tools. For example, currently, in some embodiments, the FDA does not require the disclosure of inorganic or organic sulfur content in foods. In some embodiments, inorganic sulfur, such as sulfiting agents, is commonly used as a food preservative in the United States and Europe. With the necessary food testing data, the management of USF can become simpler. In some embodiments, the use of a smart phone application, other "smart" device (e.g., PDA, PC or other computer, etc.) and/or the like can track and provide daily cumulative total of consumed inorganic sulfur and guidance for future meals to a user. In some embodiments, an analysis of animal feed consumption may also track and reveal excessive inorganic sulfur consumption resulting in oxidative stress. Such tracking can be used to regulate the consumption of inorganic sulfur to desired levels. In some embodiments, a specially-formulated feed containing lower levels of inorganic sulfur can be developed to reduce oxidative stress in animals caused by USF.

According to some embodiments, consumption of a suitable methanogenic probiotic can provide a means for reducing oxidative stress. For example, *Methanobrevibacter* spp. are methanogens that are commonly found in the human gut, but such organisms can be absent in individuals that consume elevated levels of inorganic sulfur. In some embodiments, this exclusion is most likely due to *Methanobrevibacter* spp. being catalase-negative, which makes them vulnerable to oxidative stress. In some embodiments, a specially-designed methanogenic probiotic can be developed. Such a methanogenic probiotic can include a catalase-positive *Methanobrevibacter* strain. In other arrangements, however, higher levels of catalase-negative *Methanobrevibacter* strains can be used to improve the effectiveness of the probiotic, as desired or required. In some embodiments, for example, for animals that do not have the option of a modified feed to reduce USF, a methanogen commonly found in the animal gut could be provided as a probiotic.

According to some embodiments, apheresis methods can be used to replace ROS-positive blood cells with normal blood cells. For example, in some embodiments, blood from the patient and donor can be evaluated to determine the percentage of ROS-positive blood cells by using the methods described herein and/or any other methods. Low oxidative stress blood from the donor can be processed by apheresis methods to isolate healthy white blood cells and platelets. Similarly, high oxidative stress blood from the patient can be processed by apheresis methods that remove the ROS-positive blood cells and use healthy blood cells to replace them.

Figure 3:
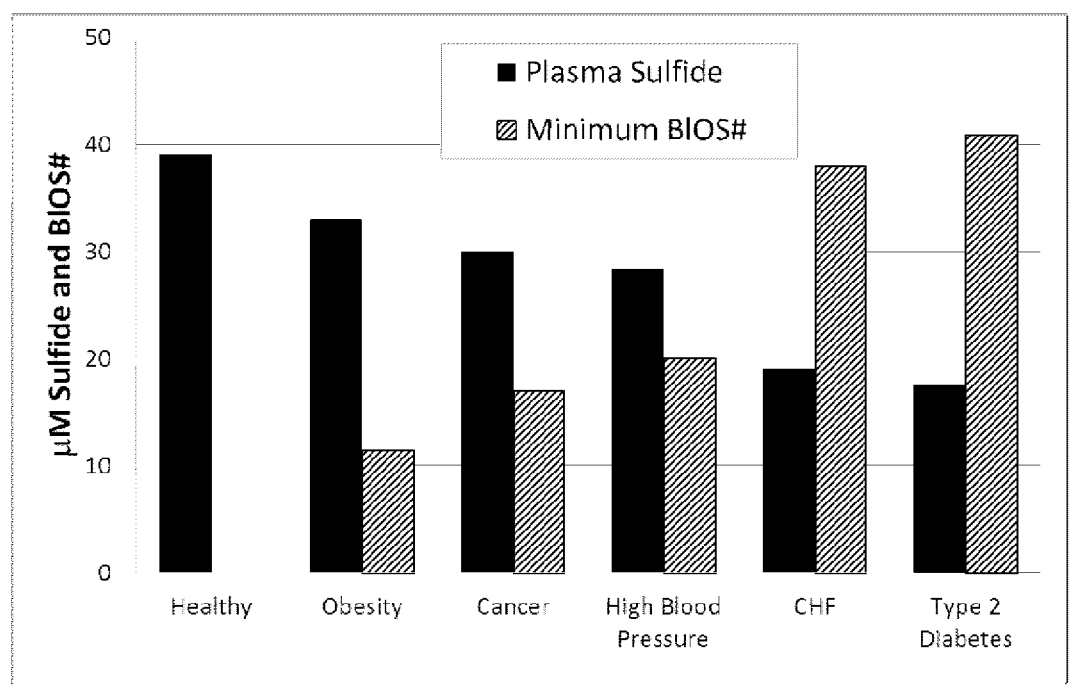
FIG. 3 is one embodiment of a chart generally illustrating a relationship of minimum BlOS # and plasma sulfide concentration for various health conditions.

According to some embodiments, guidelines for healthy and unhealthy levels of oxidative stress can be developed. For example, as illustrated in the embodiment of FIG. 3, such guidelines can be based, at least in part, on a comparison of percent ROS-positive blood cells with defined human health conditions. In some embodiments, a simple linear or other (e.g., non-linear) model can include a constant endogenous sulfide formation rate, plasma sulfide oxidation by the liver, and sulfide oxidation by ROS-positive blood cells.

For example, in some embodiments, healthy individuals exhibit a plasma sulfide concentration of about 39 µM (e.g., 35-45 µM), which corresponds to 0% ROS-positive blood cells. The additional plasma sulfide oxidation by ROS-positive blood cells, measured as BlOS #, can depress the plasma sulfide concentration. In some embodiments, certain health conditions can be observed at maximum plasma sulfide concentrations (and lower), which correspond to a minimum BlOS #, as shown, for example, in FIG. 3. In some embodiments, high blood pressure (or hypertension) is directly linked to depressed plasma sulfide concentration, which relaxes blood vessels at the healthy plasma sulfide concentration. Other health conditions can be linked to chronic or acute inflammation, which, in some instances, may be due to excessive oxidative stress caused by the presence of abnormally elevated levels of ROS-positive blood cells or high BlOS #. Subjects with arthritis can exhibit normal plasma sulfide concentrations due to excessive endogenous sulfide formation, but many also suffer from one or more inflammatory diseases.

According to some embodiments, the measurement of the BlOS # provides an advantage over plasma sulfide, since it can provide guidance on inflammatory diseases for all patients including those suffering from arthritis. The minimum BlOS # corresponding to the onset of arthritis is not shown in FIG. 3, but arthritis is thought to be due to chronic inflammation. In some embodiments, measurement of BlOS # can be advantageous compared to flow cytometry methods. For instance, flow cytometry may not account for the level of ROS production in ROS-positive blood cells. In some embodiments, the BlOS # is a relative measurement of the absolute rate of ROS production of ROS-positive blood cells. It can be a function of both blood cell concentration (WBC and platelets) and the distribution of ROS production of these blood cells. In some cases, the BlOSmax value may exceed the normal limit, which would be indicative of either excessive blood cells or high average rates of ROS production. This high BlOSmax may indicate that the patient is more vulnerable to health conditions normally associated with higher BlOS #. Abnormally high BlOSmax values could be used to adjust the BlOS # value by multiplication with the ratio of measured BlOSmax value to the normal BlOSmax value.

Increase of Oxidative Stress

According to some embodiments, low levels of oxidative stress may be beneficial. In some embodiments, the impact of virulent catalase-negative pathogens, such as *Enterococcus faecium* and Ebola Virus, may be reduced by a population, animal or human, that maintains a low level of oxidative stress. In some embodiments, in cases where the consumption of inorganic sulfur meets the minimal daily requirement to maintain health, an increase in the dietary consumption of inorganic sulfur will promote USF. In some embodiments, the consumption of a supplement containing higher levels of sulfate that releases in the large intestine would be a more attractive option when food with higher levels of inorganic sulfur is not available.

According to some embodiments, for the rapid increase of oxidative stress, intravenous (IV) method for exposing blood cells to elevated sulfide, such as NaHS, or other ROS inducing chemicals will induce the ROS response. In some embodiments, in such a method, the percent of ROS-positive blood cells is a function of the percent blood flow and the time. In some embodiments, greater times can result in higher percent ROS-positive blood cells for greater oxidative stress. In some embodiments, for example, for an IV provided to the arm, an assumed blood flow rate of 432 ml/min represents 9% of the cardiac output. In some embodiments, an exposure time of about 2.5 minutes would induce the excessive production of ROS in about 20% of the blood cells.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely provided as examples and that equivalents of such are known in the art and can be substituted for the reagents explicitly stated herein.

In some embodiments, an application for a smart phone or other computing device (e.g., PDA, tablet, laptop or other computer, etc.) can be used to calculate the daily dietary budget of inorganic sulfur that uses input data from the individual, such as height and weight, and food amount. In one embodiment, a database with inorganic sulfur content of foods would be used to calculate the amount of inorganic sulfur in the food based on the amount of the food. The daily minimal requirement of inorganic sulfur can be calculated for an individual by use of their height and weight. In some embodiments, with complete or substantial information from the user and the foods consumed, the application can provide the daily cumulative total of inorganic sulfur consumed. The application can also provide guidance on foods available at home or at a restaurant that would prevent the individual from exceeding the daily minimal requirement for inorganic sulfur. The application could also store the data for daily inorganic sulfur consumption and health related information related to oxidative stress, such as blood pressure.

In some embodiments, the use of a methanogen probiotic for the control of USF is based on the principle of competitive exclusion. In some embodiments, with USF, the SRB outcompete the methanogens in the gut due to faster specific growth rates for available hydrogen and the oxidative stress sensitivity of the existing methanogens. In order to shift this competition back towards and advantage for the methanogens, a heavy dose of viable methanogens may need to be delivered to the large intestine. In some embodiments, capsules are available that protect bacteria from release in the stomach or small intestine. In some embodiments, an optimal or clinically beneficial dosing of the methanogen probiotic is difficult to without knowledge of the abundance of the SRB and the degree of oxidative stress. In some embodiments, healthy individuals have an upper limit of SRB of about $10^9$/g wet feces with unhealthy individuals harboring $10^{11}$/g wet feces or $5\times10^{12}$ in the right colon. In some embodiments, for a probiotic regimen of $3.6\times10^{11}$ cells/day (e.g., 6 capsules with $60\times10^9$ cells each), a target gut concentration of $10^{12}$ cells in the right colon can be reached in about one week with slower increases thereafter. This calculation assumes a methanogen doubling time of 8 hours, 75% of the right colon contents wasted per day, and about 6 hours of growth per day. However, the above parameter can be modified as desired or required. In some embodiments, such assumptions are adequate to maintain the maximum SRB population with a 5.3 hour doubling time. In some embodiments, a regimen of high methanogen probiotic consumption would be needed initially to overwhelm the SRB. After this initial period of heavy consumption, a lower daily consumption rate may be needed to maintain the methanogen biomass level and prevent appreciable SRB abundance and therefore, USF. In some embodiments, microspheres of freeze-dried methanogen probiotic added to foods offer another approach to increasing the methanogen probiotic effect. In some embodiments, the methanogen probiotic method offers the advantage of minimal or no change in the individual's diet with respect to inorganic sulfur.

In some embodiments, apheresis could be used to replace ROS-positive blood cells with normal blood cells for immediate reduction of oxidative stress. The measurement of the percent ROS-positive blood cells can be used for the evaluation of the donor's and patient's blood prior to apheresis. Evaluation and monitoring of the patient's blood post-apheresis to determine reduction of oxidative stress is also possible with the methods described herein for measuring percent ROS-positive blood cells.

According to some embodiments, the dietary increase of oxidative stress requires knowledge of the inorganic sulfur content of the feed or food for animals or humans, respectively. The daily consumption of inorganic sulfur that exceeds the daily minimal requirement can, in some configurations, promote USF and therefore, oxidative stress. In some embodiments, the degree of oxidative stress is directly related to the level of inorganic sulfur consumed in excess of the daily minimal requirement. In some embodiments, an application (e.g., for a smartphone, tablet, other computing device, etc.) could be used to manage the consumption of inorganic sulfur in order to achieve a target level of oxidative stress.

According to some arrangements, the rapid onset of oxidative stress is possible through the use of IV therapy. A standard IV bag can be used to prepare a 0.9% saline or dextrose solution that also contains a NaHS concentration that delivers the target blood sulfide concentration necessary to induce the ROS response in blood cells. For example, a target blood sulfide concentration of 400 μM would require an IV bag concentration of 2,000 μM, since the IV bag flow rate is about ¼ of the blood flow rate. In some embodiments, for a cardiac output of 4,800 ml/min, the blood flow rate in the arm is 432 ml/min or 9% of the cardiac output. In one embodiment, a total IV bag volume of 270 ml or 2.5 min would induce about 20% of the blood cells to produce high levels of ROS. In some embodiments, if a lower percent of the blood cells is induced to produce ROS due to insufficient contact time or poor mixing, then a larger IV volume can be used to achieve the target percent of ROS-positive cells.

In some embodiments, a method is used to relate the percent of ROS-positive blood cells to the fluorescence intensity of the blood that corresponds to the ROS. In some embodiments, fluorescent dyes are available that react with ROS. With blood collected from the animal or human, a subsample can be exposed to elevated NaHS or other ROS inducing chemical concentration that induces the ROS response. In some embodiments, with sufficient time of no more than one hour, all of the blood cells will be induced to produce ROS. In some embodiments, a fluorescent intensity is measured for this sample that corresponds to 100% ROS-positive blood cells. With a dilution of this sample with inactivated host blood or a suitable diluent, such as saline solution, additional fluorescent intensity measurements can be made in order to develop a standard curve. In some embodiments, with this standard curve, the initial percent of ROS-positive blood cells can be determined.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combine with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

While the embodiments disclosed herein are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "collecting," "adding" or "reacting" include "instructing collecting," "instructing adding" or "instructing reacting," respectively. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 2 hours" includes "2 hours." Terms or phrases preceded by a term such as "substantially" include the recited term or phrase.

The invention claimed is:

1. A method for measuring a degree of blood oxidative stress in a subject, comprising:
    adding a first agent to a first volume of a blood sample collected from the subject, the first agent being configured to induce production of reactive oxygen species (ROS) in blood cells of the first volume;
    during a first incubation step, incubating: (1) the first volume of blood with the first agent to induce production of ROS in blood cells of the first volume, and (2) a second volume of the blood sample, wherein each of the first and second volumes contains plasma;
    during a dilution step, diluting both a first and second volumes, wherein said diluting is configured to reduce a concentration of ROS in the plasma of each of the first and second volumes;
    during a second incubation step, incubating the first and second volumes;
    following the second incubation step and during an isolation step, (1) isolating the plasma of the first volume of blood to produce a first volume of plasma, and (2) isolating the plasma of the second volume of blood to produce a second volume of plasma;
    adding a second agent to each of the first and second volumes of plasma following the isolating step, wherein adding the second agent at least partially reacts with ROS present in the first and second volumes of plasma;
    measuring a level in each of the first and second volumes of plasma indicative of reaction product formed in plasma after the second agent has reacted with ROS in each of the first and second volumes of plasma; and
    comparing the level of reaction product of the first volume of plasma to the level of reaction product of the second volume of plasma to determine a degree of blood oxidative stress in the subject.

2. The method of claim 1, wherein the isolating step is performed using centrifugation or filtration.

3. The method of claim 1, wherein the first agent comprises at least one of sodium hydrogen sulfide (NaHS), 4-demethoxydaunorubicin (idarubicin) and tert-Butyl hydroperoxide (TBHP).

4. The method of claim 1, wherein the second agent comprises a dye that is configured to react with ROS.

5. The method of claim 4, wherein the dye comprises a colorimetric dye or a fluorescent dye.

6. The method of claim 1, wherein a duration of the first incubation step is 30 minutes to 2 hours.

7. The method of claim 1, wherein a duration of the second incubation step is 5 to 30 minutes.

8. The method of claim 1, further comprising:
    providing guidance regarding a treatment for the subject based on, at least in part, the degree of blood oxidative stress in the subject.

9. The method of claim 8, wherein the guidance comprises at least one of the following: apheresis, other blood replacement procedures, dietary changes and pharmaceutical correction.

10. The method of claim 1, further comprising:
providing treatment to the subject if the degree of blood oxidative stress is above a threshold or if the degree of blood oxidative stress is indicative of disease.

11. The method of claim 10, wherein providing treatment to the subject comprises at least one of the following: apheresis, other blood replacement procedures, dietary changes and pharmaceutical correction.

12. A method for measuring a degree of blood oxidative stress in a subject, comprising:
adding a first agent to a first volume of a blood sample collected from the subject, the first agent being configured to induce production of reactive oxygen species (ROS) in blood cells of the first volume;
during a first incubation step, incubating: (1) the first volume of blood with the first agent to induce production of ROS in blood cells of the first volume, and (2) a second volume of the blood sample, wherein each of the first and second volumes contains plasma;
during a dilution step, diluting both a first and second volumes, wherein said diluting is configured to reduce a concentration of ROS in the plasma of each of the first and second volumes;
during a second incubation step, incubating the first and second volumes;
following the second incubation step and during an isolation step, (1) isolating the plasma of the first volume of blood to produce a first volume of plasma, and (2) isolating the plasma of the second volume of blood to produce a second volume of plasma;
adding a second agent to each of the first and second volumes of plasma following the isolating step, wherein adding the second agent at least partially reacts with ROS present in the first and second volumes of plasma;
measuring a level in each of the first and second volumes of plasma indicative of reaction product formed in plasma after the second agent has reacted with ROS in each of the first and second volumes of plasma; and
comparing the level of reaction product of the first and second volumes of plasma to a level of reaction products of a dilution series of at least one ROS concentration standard to determine a degree of blood oxidative stress in the subject.

13. The method of claim 12, wherein the isolating step is performed using centrifugation or filtration.

14. The method of claim 12, wherein the first agent comprises at least one of sodium hydrogen sulfide (NaHS), 4-demethoxydaunorubicin (idarubicin) and tert-Butyl hydroperoxide (TBHP).

15. The method of claim 12, wherein the second agent comprises a dye that is configured to react with ROS.

16. The method of claim 12, wherein a duration of the first incubation step is 30 minutes to 2 hours, and wherein a duration of the second incubation step is 5 to 30 minutes.

17. The method of claim 12, further comprising:
providing guidance regarding a treatment for the subject based on, at least in part, the degree of blood oxidative stress in the subject.

* * * * *